United States Patent [19]
Propp

[11] Patent Number: 5,919,146
[45] Date of Patent: *Jul. 6, 1999

[54] URINE SAMPLING AND DRAINAGE DEVICE

[75] Inventor: Donald J. Propp, Dewitt, Mich.

[73] Assignee: Tri-State Hospital Supply Corp., Howell, Mich.

[*] Notice: This patent issued on a continued prosecution application filed under 37 CFR 1.53(d), and is subject to the twenty year patent term provisions of 35 U.S.C. 154(a)(2).

[21] Appl. No.: 08/796,145

[22] Filed: Feb. 6, 1997

[51] Int. Cl.⁶ ................................ A61B 5/00; A61F 5/44
[52] U.S. Cl. ........................ 600/577; 600/573; 604/326; 604/905
[58] Field of Search .................................. 604/317, 349, 604/323, 326, 905; 600/577, 573, 579, 580

[56] References Cited

U.S. PATENT DOCUMENTS

| | | | |
|---|---|---|---|
| 4,265,118 | 5/1981 | Griesel | 600/580 |
| 4,356,012 | 10/1982 | Hofstetter | 604/324 |
| 4,411,163 | 10/1983 | White | 600/580 |
| 4,725,268 | 2/1988 | Ostensen et al. | 604/323 |
| 5,429,620 | 7/1995 | Davis | 604/905 |
| 5,569,225 | 10/1996 | Fleury | 604/349 |
| 5,616,138 | 4/1997 | Propp | 604/349 |

*Primary Examiner*—Robert A. Clarke
*Attorney, Agent, or Firm*—Fildes & Outland, P.C.

[57] ABSTRACT

A urine sampling device includes a urine collection vessel having an open end. A cap member seals the vessel open end. The cap member includes a vent to allow air displacement during fluid sampling. A connector element including a hollow piercing element is in fluid communication with the cap member. The urine sampling device is useable in combination with a urine drainage and collection device including a source tube having inlet and outlet ends for receiving and communicating urine. The source tube includes a pierceable connector for receiving the piercing element and is disposed between the source tube inlet and outlet ends. A fluid metering device including an inlet and an outlet is connected to the source tube outlet allowing gravitational fluid flow from the source tube into the metering device. A valve disposed between the pierceable connector and fluid metering device controls the gravitational fluid flow into the metering device. A receptacle in serial gravitational fluid communication with the fluid metering device outlet receives fluid from the metering device.

18 Claims, 1 Drawing Sheet

URINE SAMPLING AND DRAINAGE DEVICE

FIELD OF THE INVENTION

This invention relates to urine sampling and draining and more particularly to a gravitationally actuated sampling device for use in a system that provides urological access, fluid measurement and drainage, as well as independent sampling of most recently produced urine without exposure of the urine to contaminents or health care providers; and without exposure to needlesticks.

BACKGROUND OF THE INVENTION

It is known in the art relating to urinary catheterization to perform such catheterization to drain a patient's bladder and to obtain most recent urine samples for laboratory analysis.

Known urine drainage systems often include a urinary catheter connected to a collection/drainage device. A catheter may be maintained in or on the patient for days or weeks. Samples are typically taken from the collection device for laboratory analysis. It has long been a problem that the urine samples from the collection device are not the most recently produced urine. As a result, urine contained in the collection device has been known to become contaminated. This contaminated urine may produce unreliable laboratory analysis and unreliable biological test results.

In some known drainage systems, it is common to try to extract a sample with a syringe and an exposed hypodermic needle inserted through the wall of the drainage tubing into pooled urine in the tubing between the collection device and the urological access device; or by piercing a rubber port on the bag itself; or by opening the collection device and sucking out a sample into a syringe; or by draining some urine out of the bag into a lab sampling tube; or with infants, squeezing some urine out of a diaper into a cup and then transferring from the cup into a syringe or lab sampling tube. In addition to these various, cumbersome methods further potentially contaminating the urine itself, the nurse is exposed to both needlesticks and patient urine, and the patient might also be exposed to needlesticks.

In some other known drainage systems, it is common to exchange the collection device for a sampling device when a urine sample is desired.

In these systems, this exchange involves interrupting the urine flow to the collection device, draining the collection device, removing the collection device from its communication with the catheter, connecting the sampling device in communication with the catheter, and establishing urine flow to the sampling device. During such exchange, the sampling device is exposed to the environment and subject to contamination.

After a urine sample is collected, in like fashion, the collection device must be exchanged for the sampling device. In addition to the exchange being a complicated procedure, the exchange of the collection device typically results in the spillage of urine and its contact with the patient or health care provider.

SUMMARY OF THE INVENTION

A feature of the present invention is a urine sampling device useable in combination with an inventive urine drainage device. The sampling device allows urine collection for sampling and assures the collection of most recently produced uncontaminated urine for analysis without the need to exchange the urine collection device with the sampling device. The sampling device is a closed sterile device fluidly connectable with the urine drainage device providing a sterile receptacle for a urine sample. In addition the sampling device remains closed and is not subject to contamination until after opening which is not required until after sampling.

The present invention also provides a metering device independent of collection and sampling devices for accurately measuring urine volume output versus time. Independent flow controls on tubes connecting the devices provide for convenience and low cost construction.

Accordingly, it is an object of this invention to simplify the procedures used for urine sampling, output measurement, and bladder drainage as well as eliminate the possibility of spilling urine during the shift in procedure from sampling to draining and the possibility of contaminating the sampling device, and eliminating the possibility of needlesticks.

A more specific object of this invention is to provide a urine sampling device comprising a urine collection vessel having an open end and a cap member for sealing the vessel open end. The cap member includes a vent to allow air displacement during fluid sampling. A connector element including a hollow piercing means such as a cannula or needle is in fluid communication with the cap member.

The urine sampling device is adaptable for use in combination with a urine drainage and collection device comprising a source tube having inlet and outlet ends for receiving and communicating urine. The source tube includes a pierceable connector or septum cooperable with the piercing means for receiving the piercing means. The pierceable connector is disposed between the source tube inlet and outlet ends.

A fluid metering device including an inlet and an outlet is connected to the source tube outlet allowing gravitational fluid flow from the source tube into the metering device. A valve is disposed between the pierceable connector and fluid metering device for controlling fluid flow into the metering device. A receptacle such as a urological drainage bag is in serial gravitational fluid communication with the fluid metering device outlet for receiving fluid from the metering device.

The source tube inlet end includes at least one of a connector and an indwelling catheter. In a preferred arrangement, the source tube includes an anti-reflux valve between its inlet and outlet ends.

The metering device preferably includes a hydrophobic vent and a septum sampling port.

These and other features and advantages of the invention will be more fully understood from the following detailed description of the invention taken together with the accompanying drawings.

DETAILED DESCRIPTION OF THE INVENTION

Figure 1:
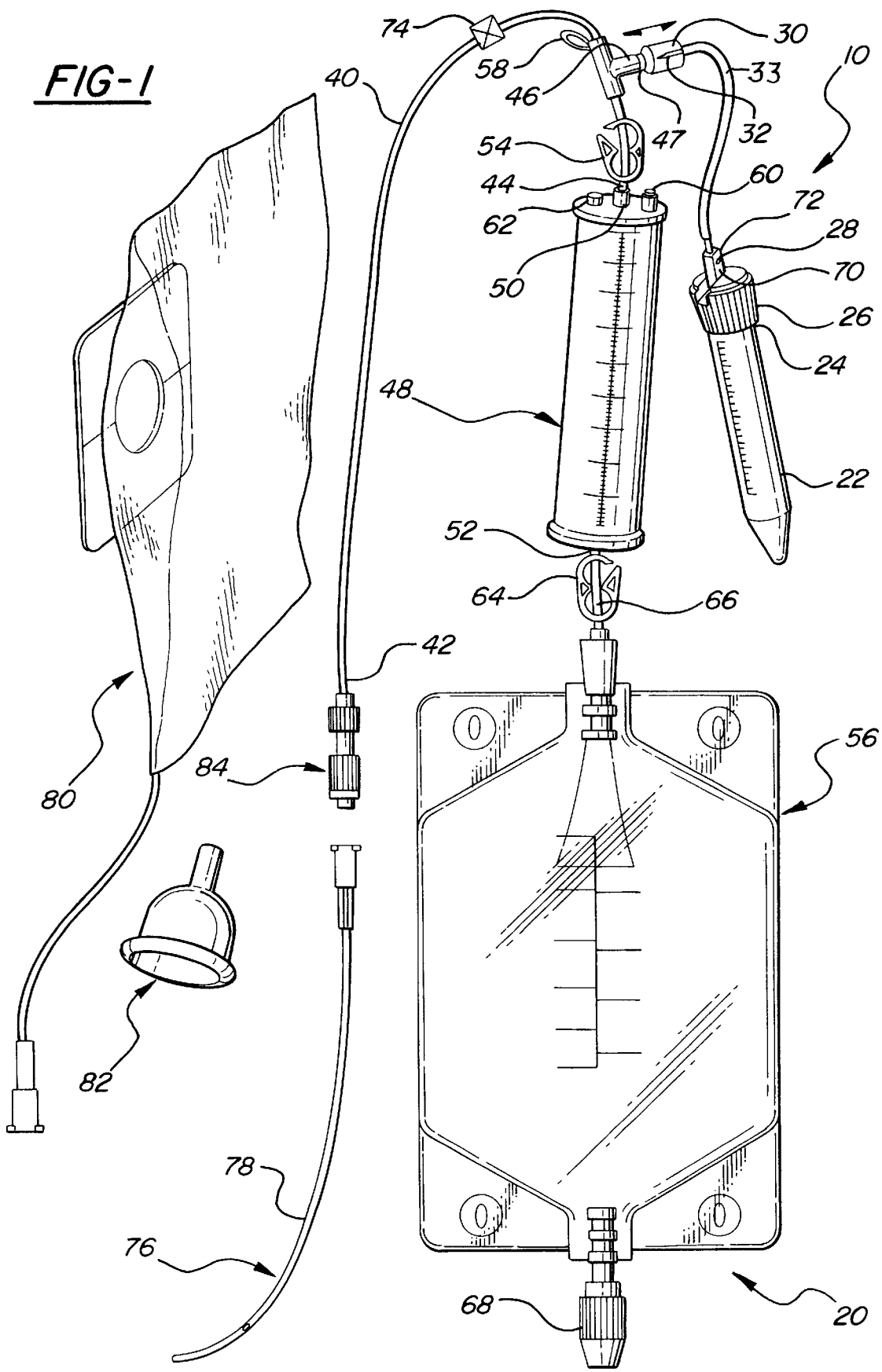
FIG. 1 is a perspective view of a urine sampling and drainage device constructed in accordance with the present invention.

Referring now to the drawing in detail, numeral 10 generally indicates a urine sampling device for use with a urine drainage device 20 as hereinafter more fully described. Urine sampling device 10 includes a urine collection vessel 22 preferably of transparent plastic or glass construction having an open end 24. A cap member 26 is fittable in threaded or snap fit fashion onto the open end 24 for sealing the vessel open end. The cap member 26 includes a vent 28 to allow air displacement out of the vessel 22 during fluid sampling.

A connector element 30 including hollow piercing means 32 such as a blunt cannula or sharp needle or luer tip is in fluid communication, through tube 33, with the cap member 26. For purposes of description, hollow piercing means 32 is illustrted as a hollow tube recessed in connector element 30.

The urine sampling device 10 is useable in combination with urine drainage and collection device 20. Urine drainage device 20 includes a source tube 40 having inlet and outlet ends 42,44 for receiving and communicating urine from a patient fluidly connected to the source tube 40. The source tube 40 includes a pierceable connector 46 including a septum 47 for receiving the piercing means 32 and is disposed between the source tube inlet and outlet ends 42,44.

A fluid metering device 48 including an inlet and an outlet 50,52, is connected to the source tube outlet 44 allowing gravitational fluid flow from the source tube 40 into the metering device 48. A valve means shown as a flow occluding clamp 54 is disposed between the pierceable connector 46 and fluid metering device 48 for controlling fluid flow into the metering device.

A receptacle 56 illustrated as a urological drainage bag is in serial gravitational fluid communication with the fluid metering device outlet 52 for receiving fluid from the metering device 48.

Source tube 40 is illustrated as a flexible plastic tube. A mounting apparatus 58 is provided for supporting the device 20 during use in a, generally, vertical hanging position allowing gravity fluid flow.

Preferably the fluid metering device 48 is a transparent chamber having graduations thereon for fluid output measurement. A preferable size range for the chamber 48 is 50 to 200 ml. Preferably, metering device 48 includes a hydrophobic vent 60 having a pore size range of 0.22 to 100 microns and a rubber septum sampling port 62.

Receptacle 56, is a disposable, flexible, thin-walled plastic urinary drainage bag or other flow receptacle, in fluid communication with the outlet end, 52 of the metering device 48. The receptacle 56 collects urine from the metering device 48 during draining of the patient's bladder. A valve or flow occluding clamp 64 may be provided on the tube 66 between the metering device 48 and receptacle 56.

Receptacle 56 may include a one-way valve such as an anti-reflux flap valve or other one-way flow control valve for preventing back flow of fluid and bacteria into the metering device 48. Receptacle 56 includes an outlet 68 to permit drainage of urine from the receptacle. Outlet 68 has an open and closed position whereby in the open position the receptacle 56 can be drained, and in a closed position urine is collectable in receptacle 56. Preferably the drainage bag 56 is of a contents size range between 300 to 2,500 ml.

In the embodiment illustrated, the sampling device 10 includes a lab sampling centrifuge tube. Cap member 26 includes a spout 70 pivotally mounted on the cap for movement from an upright, opened position to a horizontal, closed position. Cap 26 is provided with an aperture which communicates with collection vessel 22 when the cap is secured on the collection vessel as is conventionally known.

Spout 70 is provided with an aperture 72 extending through the length of the spout so that when pivoted to the upright, opened position, the aperture is aligned and communicates with the aperture in the cap 26. When the tubing on connector element 30 is pulled out of aperture 72 and spout 70 is in the horizontal, closed position, the spout lies in the slot located in cap 26 and aperture 72 is no longer aligned with the aperture in the cap and there is no communication. Aperture 72 is in fluid communication with connector element 30 for easily mounting the sampling device 10 to the pierceable connector 46 on the source tube 40.

The vent 28 is illustrated as being provided in the spout 70. As illustrated, vent 28 is an aperture extending through the side of the spout 70 so that when the spout is in the upright, opened position, the vent aperture is in communication with the aperture in the cap. Preferably, vent 28 includes a hydrophobic vent filter. Vent 28 vents the sampling device 10 during fluid collection for sampling as is readily apparent. In like fashion, when the spout 70 is in the horizontal closed position, the vent 28 is no longer in communication with the aperture in the cap and sealed against leakage.

In a preferred embodiment, the source tube 40 includes an anti-reflux valve 74, to prevent reflux of urine towards the bladder.

A urological access device 76, such as a urethral indwelling catheter 78, genitalia covering collection bag 80, or external male condom catheter 82 is connectable to the inlet end 42 of the source tube 40. The urological access device 76 provides bladder access for the drainage device 20. Although the access device 76 is illustrated as being detachably connectable via a luer connector 84 to the source tube 40, the access device 76 can be non-removably bonded to the source tube.

The present devices 10,20 are typically provided as a preassembled sterile kit for continuous output catheterization for acute or chronic bladder drainage. Such a kit is particularly well suited for neonatal and pediatric care use. In such a system, the access device 76 is applied to the patient to begin drainage. Fluid received by the access device 76 is communicated through the source tube 40.

To take a urine sample, the piercing means 32 of the sampling device 10 is inserted into the septum 47 of the drainage device to fluidly connect the sampling device to the drainage device as the pierceable commector 46 is connected to connector element 30. Clamp 54 is then closed to allow gravity flow of the urine from the source tube 40 into the sampling device 10. When a sufficient sample has been received, clamp 54 is opened to allow drainage toward the receptacle 56 and the piercing means 32 is simply removed from the pierceable connector 46.

When another sample is needed, the procedure is repeated with another sterile sampling device 10 or vessel 22. The most recently produced urine is easily sampled without the complications and possibility of urine contamination of heretofore systems.

The connector element 30 may also include a shrouded cannula, a shrouded blunt cannula, a shrouded blunt cannula with lock on means, a shrouded needle, or a shrouded needle with lock on means. Likewise, the pierceable connector 46 may include a complementary non pre-slit septum or a pre-slit septum.

In another embodiment, the pierceable connector may be a septum having the piercer inside of it (the septum) and is actuated by the end of an ordinary male luer tip pushing the septum into it's (the septum's) internal hollow piercer. In such an embodiment, the hollow piercer comes all the way through the septum and into the ID of the male luer fitting. In such an embodiment, the connector element is either a male luer slip or a male luer lock fitting in fluid communication with the cap member 26.

Although the invention has been described by reference to a specific embodiment, it should be understood that numerous changes may be made within the spirit and scope of the inventive concepts described. Accordingly, it is intended that the invention not be limited to the described embodiment, but that it have the full scope defined by the language of the following claims.

What is claimed is:

1. A urine sampling device comprising:
    a urine collection vessel having an open end;
    a cap member sealing said vessel open end, said cap member including a spout having an aperture extending therethrough; said spout being mounted for pivotal movement between an upright opened position and a horizontal closed position; said spout including a vent to allow air displacement during fluid sampling;
    a connector element for connecting to an associated connector element;
    a hollow piercing means mounted in said connector element; and
    a tube disposed for fluid communication between said hollow piercing means and said spout and spacing said connector element and cap member.

2. The urine sampling device as in claim 1 wherein said hollow piercing means is a cannula.

3. The urine sampling device as in claim 1 wherein said hollow piercing means is a needle recessed in said connector element.

4. The urine sampling device as in claim 1 wherein said connector element is a male luer fitting.

5. The urine sampling device of claim 1 in combination with a urine drainage and collection device comprising:
    a source tube having inlet and outlet ends for receiving and communicating urine; said source tube including a pierceable connector defining said associated connector element and including a septum for receiving said piercing means and disposed between said source tube inlet and outlet ends;
    a fluid metering device including an inlet and an outlet, said inlet being connected to the source tube outlet allowing gravitational fluid flow from said source tube into said metering device;
    valve means disposed between said pierceable connector and fluid metering device for controlling fluid flow into said metering device; and
    a receptacle in serial gravitational fluid communication with said fluid metering device outlet for receiving fluid from said metering device.

6. The device of claim 5 wherein said valve means is a flow occluding clamp.

7. The device of claim 5 wherein said pierceable connector is a septum.

8. The device of claim 5 including valve means disposed between said fluid metering device and receptacle for controlling fluid flow out of said metering device.

9. The device of claim 8 wherein said valve means is a flow occluding clamp.

10. The device of claim 5 wherein said source tube inlet end includes at least one of a luer connector and an indwelling catheter.

11. The device of claim 5 wherein said source tube inlet end includes a connector.

12. The device of claim 5 wherein said source tube includes an anti-reflux valve between said inlet and outlet ends.

13. The device of claim 5 wherein said metering device includes a hydrophobic vent.

14. The device of claim 5 wherein said metering device includes a septum sampling port.

15. The device of claim 5 wherein said receptacle is a urological drainage bag.

16. The device of claim 15 wherein said drainage bag includes an anti-reflux flap valve.

17. The device of claim 5 wherein said source tube inlet end includes at least one of a luer connector and an indwelling catheter.

18. The device of claim 5 wherein said receptacle is a urological drainage bag.

* * * * *